(12) United States Patent
Mahmood et al.

(10) Patent No.: US 6,692,761 B2
(45) Date of Patent: Feb. 17, 2004

(54) SCAFFOLD FOR TISSUE ENGINEERING CARTILAGE HAVING OUTER SURFACE LAYERS OF COPOLYMER AND CERAMIC MATERIAL

(75) Inventors: Tahir Mahmood, Cambridge, MA (US); Jens Uwe Riesle, Amsterdam (NL); Clemens Antoni van Blitterswijk, Hekendorp (NL)

(73) Assignee: IsoTis N.V., Bilthoven (NL)

( * ) Notice: Subject to any disclaimer, the term of this patent is extended or adjusted under 35 U.S.C. 154(b) by 0 days.

(21) Appl. No.: 09/946,242

(22) Filed: Sep. 5, 2001

(65) Prior Publication Data

US 2002/0009477 A1 Jan. 24, 2002

Related U.S. Application Data

(63) Continuation of application No. 09/497,987, filed on Feb. 4, 2000.

(30) Foreign Application Priority Data

Feb. 10, 1999 (EP) .............................................. 99200396

(51) Int. Cl.⁷ ............................ A61F 2/00; C12N 11/14; C12N 11/08; C12N 5/06; C12N 5/08
(52) U.S. Cl. ....................... 424/426; 424/93.7; 435/176; 435/180; 435/182; 435/395
(58) Field of Search ................................ 424/423, 426, 424/93.7; 435/174, 176, 180, 182, 395

(56) References Cited

U.S. PATENT DOCUMENTS 5,980,948 A     11/1999   Goedemoed et al. ........ 424/489
6,228,117 B1 *   5/2001   De Bruijn et al. ....... 623/16.11

FOREIGN PATENT DOCUMENTS

EP      0 469 070        2/1992
EP      1 002 859        5/2000

* cited by examiner

Primary Examiner—David M. Naff
(74) Attorney, Agent, or Firm—Banner & Witcoff, Ltd.

(57) ABSTRACT

A biodegradable, biocompatible porous matrix as a scaffold for tissue engineering cartilage is formed of a copolymer of a polyalkylene glycol and an aromatic polyester such as a polyethylene glycol/polybutylene terephtalate copolymer. A ceramic coating such as a calcium phosphate coating may be provided on the scaffold by soaking the scaffold in a solution containing calcium and phosphate ions. A composite scaffold which is preferably a two-layer system may be formed having an outer surface of a layer of the porous matrix formed of the copolymer, and an outer surface of a layer of a ceramic material. The composite scaffold may be prepared by casting the copolymer on top of the ceramic material in a mould. Cells are preferably seeded on the scaffold prior to implanting, and the scaffold may contain bioactive agents that are released on degradation of the scaffold in vivo.

18 Claims, No Drawings

SCAFFOLD FOR TISSUE ENGINEERING CARTILAGE HAVING OUTER SURFACE LAYERS OF COPOLYMER AND CERAMIC MATERIAL

This is a continuation of U.S. patent application Ser. No. 09/497,987, filed on Feb. 4, 2000; which in turn claims the benefit of the filing date of European Patent Application No. EP 99200396.2, filed on Feb. 10, 1999.

BACKGROUND OF THE INVENTION

1. Field of the Invention

The invention relates to a scaffold for use in a method of tissue engineering cartilage.

2. Description of the Related Art

The inability of articular cartilage for self-repair is a major problem in the treatment of patients who have their joints damaged by traumatic injury or suffer from degenerative conditions, such as arthritis or osteoarthritis. Examples of currently employed treatments include subchondral drilling and abrasion. However, these treatments are hardly effective in the long term, as they do not promote formation of new or replacement cartilage tissue, or cartilage-like tissue. Instead, these treatments lead to scar or fibrous tissue, which cannot withstand joint loading in the long term. Thus, although the condition of patients treated by using these conventional techniques initially improves, eventually it will deteriorate, possibly leading to osteoarthritis.

Another therapy conventionally relied on for treating loss of cartilage is replacement with a prosthetic material, such as silicone for cosmetic repairs, or metal alloys for joint relinement. Placement of prostheses is commonly associated with significant loss of underlying tissue and bone without recovery of the full function allowed by the original cartilage, as well as the irritating presence of a foreign body. Other long term problems associated with a permanent foreign body can include infection, erosion and instability.

Recently, new approaches to cartilage tissue repair have been proposed. These approaches are based on implanting or injecting expanded autologous cells per se into a defect in a patient's cartilage tissue. However, it has meanwhile been accepted that the majority of the thus implanted cells will not sustain. Also, this approach is only feasible for a relatively narrow group of patients.

Even more recent, it has been proposed in EP-A-0 469 070 to use a biocompatible synthetic polymeric matrix seeded with chondrocytes, fibroblasts or bone-precursor cells as an implant for cartilaginous structures. It is taught that it is essential that the polymeric matrix is formed of fibers or a fibrous mesh in order to provide free exchange of nutrients and waste products to the cells attached to the matrix. This free exchange is described to be particularly relevant in the stage after implantation wherein vascularization of the implant has not yet taken place. The material used for providing the polymeric matrix is a biocompatible synthetic material. The only specifically mentioned material is polyglactin 910, a 90:10 copolymer of glycolide and lactide.

SUMMARY OF THE INVENTION

The present invention aims to provide an improved scaffold for tissue engineering cartilage. It is an object to provide an artificial matrix which is highly suitable to serve as a temporary scaffold for cellular growth and implantation of cartilage. The matrix should be biodegradable and non-toxic and enable cell growth both in vivo and in vitro. It is a further object that the scaffold can provide sufficient mechanical strength for it to be utilized for cell growth to replace degenerated cartilage in joints, and desirably also to withstand joint loading. It should further be possible to design the scaffold such that it is suitable to replace hyaline or elastic cartilage in plastic and reconstructive surgery.

DETAILED DESCRIPTION OF THE INVENTION

Surprisingly, it has been found that the above objectives are fulfilled by using a porous matrix of a specific polymeric material as a scaffold for engineering cartilage tissue. Thus, the invention relates to the use of a biodegradable, biocompatible porous matrix as a scaffold for tissue engineering cartilage, which matrix is formed of a copolymer of a polyalkylene glycol and an aromatic polyester.

The material used as a scaffold in accordance with the invention meets all the above requirements for use in cartilage repair or replacement. In particular, said material provides superior mechanical strength so that the scaffold is able to withstand joint loading to a degree which is not attainable using a fibrous structure.

Furthermore, the specific polymeric material on which the present scaffold is based has hydrogel properties and allows for diffusion through the material itself, in addition to diffusion through its porous structure. Of course, this feature is highly advantageous when cells are seeded onto the scaffold and are cultured thereon, as it enables a very efficient transport of nutrient and waste materials from and to the cells. Secondly, the material closely mimics the structure and properties of natural cartilage, which, containing 80% water, is also a hydrogel. Furthermore, the swelling behavior of the specific polymeric material allows for optimal fixation of the structure in a defect when it is implanted without cells seeded thereto in vitro, A matrix to be used as a scaffold in accordance with the invention is biodegradable and biocompatible. In the context of the present invention, the term biocompatible is intended to refer to materials which may be incorporated into a human or animal body substantially without unacceptable responses of the human or animal. The term biodegradable refers to materials which, after a certain period of time, are broken down in a biological environment. Preferably, the rate of breakdown is chosen similar or identical to the rate at which the body generates autogenous tissue providing sufficient mechanical strength to replace the implant of which the biodegradable material is manufactured.

In accordance with the invention, the matrix has a slower rate of degradation in a biological environment than the copolymers of glycolide and lactide which are preferred according to the above discussed EP-A-0 469 070, ensuring mechanical support over the whole regeneration period in vivo before the extracellular matrix synthesized by cells seeded onto the scaffold, or by cells of the surrounding tissue present in vivo, takes over the mechanical function.

Further, the present matrix is porous (i.e. non-fibrous). This means that the matrix is a substantially homogeneous, solid structure, provided with small holes (pores), which enable diffusion of nutrients and waste products. As opposed to a fibrous structure, which is composed of different elements (fibers), the present porous matrix is a continuous structure, substantially composed of one element, comprising distinct compartments. It is preferred that the pores in the present matrix are interconnected.

Preferably, the matrix has a macroporosity between 30 and 99%, more preferably between 60 and 95%. The pores in the matrix preferably have a diameter of between 0.1 and 2000 µm, more preferably between 1 and 1000 µm. The macroporosity and the diameter of the pores will be chosen such that, on the one hand, sufficient diffusion of nutrients and waste products can take place, and, on the other hand, sufficient mechanical strength is provided by the matrix.

As has been mentioned, the present scaffold is formed of a specific class of polymeric materials having hydrogel properties. This is the class of copolymers of a polyalkylene glycol and an aromatic polyester. Preferably, these copolymers comprise 40–80 wt. %, more preferably 50–70 wt. % of the polyalkylene glycol, and 60–20 wt. %, more preferably 50–30 wt. % of the aromatic polyester. A preferred type of copolymers according to the invention is formed by the group of block copolymers.

Preferably, the polyalkylene glycol has a weight average molecular weight of from 150 to 4000, more preferably of 200 to 1500. The aromatic polyester preferably has a weight average molecular weight of from 200 to 5000, more preferably of from 250 to 4000. The weight average molecular weight of the copolymer preferably lies between 20,000 and 200,000, more preferably between 50,000 and 120,000. The weight average molecular weight may suitably be determined by gel permeation chromatography (GPC). This technique, which is known per se, may for instance be performed using tetrahydrofuran as a solvent and polystyrene as external standard.

In a preferred embodiment, the polyalkylene glycol component has units of the formula —OLO—CO—Q—CO—, wherein O represents oxygen, C represents carbon, L is a divalent organic radical remaining after removal of terminal hydroxyl groups from a poly(oxyalkylene)glycol, and Q is a divalent organic radical.

Preferred polyalkylene glycols are chosen from the group of polyethylene glycol, polypropylene glycol, and polybutylene glycol and copolymers thereof, such as poloxamers. A highly preferred polyalkylene glycol is polyethylene glycol.

The terms alkylene and polyalkylene generally refer to any isomeric structure, i.e. propylene comprises both 1,2-propylene and 1,3-propylene, butylene comprises 1,2-butylene, 1,3-butylene, 2,3-butylene, 1,2-isobutylene, 1,3-isobutylene and 1,4-isobutylene (tetramethylene) and similarly for higher alkylene homologues. The polyalkylene glycol component is preferably terminated with a dicarboxylic acid residue —CO—Q—CO—, if necessary to provide a coupling to the polyester component. Group Q may be an aromatic group having the same definition as R, or may be an aliphatic group such as ethylene, propylene, butylene and the like.

The polyester component preferably has units —O—E—O—CO—R—CO—, wherein O represents oxygen, C represents carbon, E is a substituted or unsubstituted alkylene or oxydialkylene radical having from 2 to 8 carbon atoms, and R is a substituted or unsubstituted divalent aromatic radical.

In a preferred embodiment, the polyester is chosen from the group of polyethylene terephtalate, polypropylene terephtalate, and polybutylene terephtalate. A highly preferred polyester is polybutylene terephtalate.

It is believed that the use of a copolymer of polyethylene glycol, having a weight average molecular weight of between 800 and 1200 (preferably 1000) and polybutylene terephtalate in a weight ratio of between 65 to 35 and 75 to 25 (preferably 70 to 30) may lead to a faster proliferation of cells, such as chondrocytes, seeded on a scaffold of said copolymer.

The preparation of the copolymer will now be explained by way of example for a polyethylene glycol/polybutylene terephtalate copolymer. Based on this description, the skilled person will be able to prepare any desired copolymer within the above described class. An alternative manner for preparing polyalkylene glycol/polyester copolymers is disclosed in U.S. Pat. No. 3,908,201.

A polyethylene glycol/polybutylene terephtalate copolymer may be synthesized from a mixture of dimethyl terephtalate, butanediol (in excess), polyethylene glycol, an antioxidant and a catalyst. The mixture is placed in a reaction vessel and heated to about 180° C., and methanol is distilled as transesterification proceeds. During the transesterification, the ester bond with methyl is replaced with an ester bond with butylene. In this step the polyethyene glycol substantially does not react. After transesterification, the temperature is raised slowly to about 245° C., and a vacuum (finally less than 0.1 mbar) is achieved. The excess butanediol is distilled and a prepolymer of butanediol terephtalate condenses with the polyethylene glycol to form a polyethylene/polybutylene terephtalate copolymer. A terephtalate moiety connects the polyethylene glycol units to the polybutylene terephtalate units of the copolymer and thus such copolymer also is sometimes referred to as a polyethylene glycol terephtalate/polybutylene terephtalate copolymer (PEGT/PBT copolymer).

A porous structure of the polymeric material may be obtained by any known method, such as salt leaching or sintering. In principle, any combination of techniques, such as phase inversion, freeze drying and salt leaching may be used.

In a salt leaching procedure, the scaffold material may be subjected to a solvent casting procedure, wherein a substrate is formed by liquefying the material in a suitable solvent containing salt particles having a suitable particle size to acquire the desired pore size. The salt/polymer solution may then be cast on a plate using a substrate-casting apparatus fixed at a certain height finally leading to the desired thickness of the structure to be formed. The salt particles are then leached out of the copolymer by washing with, for instance (distilled) water.

It is also possible to use a viscous polymer gel in the salt leaching procedure, instead of a polymeric solution. In that case, the first step of the procedure is the preparation of a relatively concentrated polymer solution (preferably comprising at least 50 wt. % of the polymer) at elevated temperatures, such as from 60 to 120° C. Preferred solvents have a relatively high boiling point, and are miscible with water. An example of a solvent which has been found to particular good results is N-methylpyrrolidone. In the second step of the procedure, salt particles are added to the polymer solution. Subsequently, the solution is transferred into a mould, having the desired shape and size of the scaffold to be formed, and is cooled to room temperature. Upon cooling, a stable polymer gel is formed. Placement of the gel in demineralized water leads to removal of the solvent and the salt, resulting in a stable porous material.

In a sintering procedure, the scaffold material may be placed into a mold and subsequently heated under pressure to a temperature below the melting point of the material. Releasing the pressure and cooling the material yields a sintered product. The skilled person may, based on his general knowledge, adapt the conditions during the sintering procedure such that the desired porous structure is obtained.

Yet another advantage of the specific polymeric material of which the present scaffold is formed is that it is possible to incorporate bioactive agents in said material, which agents are slowly released upon degradation of the material in vivo. In this regard, reference is made to the U.S. Pat. No. 5,980,948, the contents of which are incorporated herein by reference.

In a preferred embodiment, the outer surface of the scaffold is partly or completely provided with a ceramic coating. Preferably, the ceramic coating is a calcium phosphate coating. It has been found that the presence of a ceramic coating is highly beneficial to the attachment of cells to the scaffold. The calcium phosphate may be applied to the polymeric material by soaking said material into a highly concentrated calcifying solution at low temperature. The calcifying solution is preferably composed of at least is calcium and phosphate ions, and optionally of magnesium, carbonate, sodium and chloride ions, which are dissolved into water by bubbling carbon dioxide gas. During the natural release of carbon dioxide gas or its exchange with air, the pH of the calcifying solution is increased and the saturation is raised until the nucleation of carbonated calcium phosphate crystals on the surface of the scaffold. The process of bubbling/releasing $CO_2$ gas through or from the calcifying solution can be repeated until a sufficient thickness of the coating has been reached. In general, the thickness of the ceramic layer will be between 0.1 and 20 $\mu$m. It is preferred, that the ceramic coating is designed such that it has its beneficial effect during the seeding of cells onto the scaffold, and during the subsequent in vitro culturing of said cells. It is further preferred, that, by the time the scaffold is to be implanted into a patient's body, the ceramic coating has substantially disappeared. This may for instance be accomplished through the presence of the cells or culture medium, e.g. by dissolution.

Under certain conditions, particularly when the scaffold is intended to be used in the treatment of full-thickness cartilage defects, comprising cartilage as well as bone, it has been found advantageous to use a composite scaffold comprising a first part which has an outer surface of a polymeric material, of the above discussed type, and second part which has an outer surface of a ceramic material. The composite matrix preferably is a two-layer system, wherein the ceramic part mimics the function of bone, and the polymeric part mimics the function of cartilage. Thus, the composite matrix mimics the nature of both cartilage and bone tissue. Furthermore, the ceramic outer surface facilitates adhesion of cells to the scaffold both in vitro and in vivo.

The first part of the composite matrix, is preferably substantially in its entirety formed of a copolymer of the above discussed type. The second part of the composite matrix may be substantially completely formed of a ceramic material. Examples of suitable ceramic materials include calcium phosphate, calcium carbonates, and sodium calcium phosphates. Particularly suitable ceramic materials are chosen from the group of octacalcium phosphate, apatites, such as hydroxyapatite and carbonate apatite, whitlockites, such as $\alpha$-tricalcium phosphate, $\beta$-tricalcium phosphate, sodium calcium phosphate, and combinations thereof. It is also possible that the second part is formed of a different material, but coated with a ceramic material as set forth herein above. The said different material may be any type of polymeric material, preferably the above discussed copolymer of a polyalkylene glycol and an aromatic ester, or another suitable material, such as Bioglass or a glass-ceramic.

In a preferred embodiment, a dense layer, preferably of the above discussed copolymer of a polyalkylene glycol and an aromatic ester, is applied between the polymeric and ceramic parts to avoid movement of cells from one part to the other.

The composite may be prepared in any suitable manner, for instance by providing a mould having the desired shape of the composite scaffold. The ceramic part of the composite, which is prepared separately, may be placed in the mould, and the polymeric layer may be cast on top of the ceramic part, e.g. by injection moulding. It is also possible to apply the polymeric part in the form of a polymer-salt solution, which is used in the above described salt leaching procedure for achieving the desired porosity. Optionally, the dense layer may be applied onto the ceramic part first. A good attachment is obtained between the ceramic and polymeric parts of the composite as the polymeric material will invade the pores of the ceramic part to some extent during injection moulding.

A scaffold based on a biodegradable, biocompatible, porous matrix as described above, which is of course also encompassed by the present invention, may be used in tissue engineering cartilage with or without cells seeded thereon in vitro. The scaffold may be processed to have a particular desired form in any known manner. The matrix being formed of a polymeric material having hydrogel properties, the swelling behavior or the scaffold allows for swell fixation of the implant in a defect in cartilage tissue into which it is implanted. This swell fixation is specifically advantageous when the scaffold is implanted cell free. The extent of swelling can suitable be controlled by adjusting the composition of the polymeric material.

In a preferred embodiment, the scaffold is seeded with cells prior to its implantation. The cells may be any type of cells commonly occurring in natural cartilage or any type of cells capable of differentiating into cells commonly occurring in natural cartilage. Preferred cell types are chondrocytes, bone-precursor cells, stem cells, and cells of periosteum or perichondrium tissues. These cells may also be used in their crude form, e.g. in the form of bone marrow, comprising more than one cell type or even extracellular matrix. It is further preferred that the cells are autologous cells, thus minimizing, or even excluding, the chance of rejection responses in or disease transmission (e.g. HIV) to the patient treated with the present scaffold.

The seeding may be carried out in any known manner, for instance by static seeding. It is preferred, however, that the cells are seeded dynamically as has been described in co-pending European patent application 98203774.9, which is incorporated herein by reference. Subsequent to the seeding process, the cells are preferably cultured in vitro, allowing for a sufficient degree of proliferation and/or differentiation of the cells. The period required for culturing may vary broadly and range between one hour and several months, dependent on the number of seeded cells and the size of the implant required.

The invention further relates to the use of the above scaffold as a medical implant in cartilage repair. This use may specifically apply in cases of damaged cartilage in a patient as a result of inflammation, trauma, aging, or wherein the cartilage is congenitally defective.

The invention will now be elucidated by the following, non-restrictive example.

EXAMPLE

Human chondrocytes were isolated from articular cartilage and seeded on a porous Polyactive scaffold (55/45(300), 1.55 cm diameter, 300 $\mu$m thick discs, macroporosity 75%). The chondrocytes were dynamically seeded onto the scaffold for 24 hours and cultured for 20 days in flasks using a magnetic stirrer at 45 rpm. Thus, both the seeding and the culturing were performed under dynamic conditions. The culture medium comprised Dulbecco's modified Eagle medium (DMEM) containing 4.5 g/L glucose, 584 mg/L glutamine, 10% Fetal Bovine Serum (F, 50 U/ML penicillin), 50 µg/mL streptomycin, 10 mM N-2hydroxyethylpiperazine N'-2-ethanesulfonic acid (HEPES), 0.1 mM non-essential amino acids, 0.4 mM proline and 50 µg/mL ascorbic acid.

Samples were taken for SEM (Scanning Electron Microscopy) and LM (Light Microscopy) analysis 3, 10 and 20 days after seeding. After 3 days, both SEM and stereo LM (allowing for 3-dimensional analysis) showed pronounced cell attachment and ingrowth. After 20 days, homogeneous cell distribution within the matrix and ECM formation were observed.

What is claimed is:

1. A method for repairing cartilage comprising selecting a composite scaffold for tissue engineering cartilage wherein the scaffold has an outer surface of a layer of a biodegradable, biocompatible, porous matrix formed from a copolymer comprising a polyalkylene glycol and an aromatic polyester, and an outer surface of a layer of a ceramic material, and implanting the scaffold.

2. The method according to claim 1, wherein the matrix comprises chondrocytes, bone-precursor cells, stem cells or cells of periosteum or perichondrium tissue.

3. The method according to claim 1, wherein the polyalkylene glycol comprises polyethylene glycol and the aromatic polyester comprises poly(butyleneterephthalate).

4. The method according to claim 1, wherein the matrix comprises a calcium phosphate coating.

5. The method according to claim 1, wherein the ceramic material is calcium phosphate.

6. The method according to claim 1, wherein the ceramic material is selected from the group consisting of octacalcium phosphate, apatites, whitlockites, and combinations thereof.

7. The method according to claim 1, wherein the ceramic material is selected from the group consisting of hydroxyapatite, α-tricalcium phosphate, β-tricalcium phosphate, sodium calcium phosphate, and combinations thereof.

8. The method of claim 1, wherein the layer of the matrix is a substrate on which the layer of the ceramic material is formed.

9. The method of claim 1, wherein the layer of the matrix is formed on a substrate and the layer of the ceramic material is formed on a substrate.

10. A method for making a composite scaffold for repairing cartilage comprising selecting a biodegradable, biocompatible, copolymer comprising a polyalkylene glycol and an aromatic polyester and selecting a ceramic material and forming a composite scaffold having an outer surface of a layer of a matrix formed from the copolymer, and an outer surface of a layer of the ceramic material, wherein the composite scaffold is suitable for implantation.

11. The method according to claim 10, wherein the matrix comprises chondrocytes, bone-precursor cells, stem cells or cells of periosteum or perichondrium tissue.

12. The method according to claim 10, wherein the polyalkylene glycol comprises polyethylene glycol and the aromatic polyester comprises poly(butyleneterephthalate).

13. The method according to claim 10, wherein the matrix comprises a calcium phosphate coating.

14. The method according to claim 10, wherein the ceramic material is calcium phosphate.

15. The method according to claim 10, wherein the ceramic material is selected from the group consisting of octacalcium phosphate, apatites, whitlockites, and combinations thereof.

16. The method according to claim 10, wherein the ceramic material is selected from the group consisting of hydroxyapatite, α-tricalcium phosphate, β-tricalcium phosphate, sodium calcium phosphate, and combinations thereof.

17. The method of claim 10, wherein the layer of the matrix is a substrate on which the layer of the ceramic material is formed.

18. The method of claim 10, wherein the layer of the matrix is formed on a substrate and the layer of the ceramic material is formed on a substrate.

* * * * *